United States Patent
Gradle et al.

(10) Patent No.: US 7,153,527 B2
(45) Date of Patent: *Dec. 26, 2006

(54) IODINE-PROPYLENE GLYCOL TEAT DIP

(75) Inventors: Charles D. Gradle, Berwyn, IL (US); Alejandro O. Dee, Roselle, IL (US)

(73) Assignee: WestfaliaSurge, Inc., Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/147,005

(22) Filed: Jun. 7, 2005

(65) Prior Publication Data

US 2005/0233006 A1 Oct. 20, 2005

Related U.S. Application Data

(63) Continuation of application No. 09/563,290, filed on May 3, 2000, now Pat. No. 6,902,747.

(51) Int. Cl.
*A01N 59/12* (2006.01)
*A01N 31/02* (2006.01)
*A61K 33/18* (2006.01)
*A61K 31/047* (2006.01)

(52) U.S. Cl. ............ 424/668; 424/667; 424/669; 424/670; 424/671; 424/672; 514/738; 422/29; 422/37

(58) Field of Classification Search ........ 424/667–672; 514/738; 422/29, 37
See application file for complete search history.

(56) References Cited

U.S. PATENT DOCUMENTS

| 2,863,798 | A | | 12/1958 | Shelanski et al. |
| 3,728,449 | A | | 4/1973 | Cantor et al. |
| 4,012,504 | A | | 3/1977 | Eckols |
| 5,643,608 | A | * | 7/1997 | McKinzie et al. .......... 424/667 |
| 5,919,471 | A | | 7/1999 | Saferstein et al. |
| 6,432,426 | B1 | * | 8/2002 | Kessler ...................... 424/401 |
| 6,699,907 | B1 | | 3/2004 | Dee et al. |
| 6,902,747 | B1 | * | 6/2005 | Gradle et al. ............... 424/668 |

FOREIGN PATENT DOCUMENTS

| EP | 0094219 A1 | 11/1983 |
| WO | WO 00/13506 | 3/2000 |
| WO | WO 02/28180 A2 | 4/2002 |

OTHER PUBLICATIONS

Berkelman et al., Increased Bactericidal Activity of Dilute Preparations of Povidone-Iodine Solutions, J. of Clinical Microbiology, vol. 15, No. 4, pp. 635-639 (1982).

Pankey et al., Uptake on Postmilking Teat Antisepsis, J. of Diary Science, vol. 67, No. 6, pp. 2281-2288 (1984).

Fox et al., *Staphylococcus aureus* Colonization of Teat Skin as Affected by Postmilking Teat Treatment . . . , J. of Dairy Science, vol. 77, No. 8, pp. 1336-1353 (1994).

Form PCT/ISA/220, Notification of Transmittal of the International Search Report or the Declaration received Oct. 9, 2001, 6pgs & 210 for PCT/US01/14291.

Form PCT/IPEA/416, Notification of Transmittal of International Preliminary Examination Report, Aug. 27, 2003, 7pgs & 409 for PCT/US01/14291.

* cited by examiner

*Primary Examiner*—John Pak
(74) *Attorney, Agent, or Firm*—Smith Law Office

(57) ABSTRACT

A teat dip composition comprising from about 0.1% to about 2% iodine by weight of the composition on a formulation basis and form about 45% to about 99.9% propylene glycol by weight of the composition on a formulation basis, and a method of using such composition to treat mastitis.

3 Claims, No Drawings

IODINE-PROPYLENE GLYCOL TEAT DIP

This application is a continuation of application Ser. No. 09/563,290 filed May 3, 2000 and issued as U.S. Pat. No. 6,902,747 on Jun. 7, 2005, the disclosure of which is incorporated by reference herein.

FIELD AND BACKGROUND OF THE INVENTION

This invention relates generally to antiseptic teat dips, and more particularly to a teat dip including iodine as an antimicrobial agent and propylene glycol as a primary carrier for the iodine.

Mastitis is a major world-wide problem for operations involving dairy animals, such as cows and goats. It is estimated that mastitis results in a per annum production loss to dairy farmers in the United States alone of between two and three billion dollars. Therefore, control of mastitis is of great concern to those in the dairy industry.

Mastitis is caused by infections of the mammary, or milk-producing glands by a broad spectrum of pathogenic microorganisms, such as *Staphylococcus aureus, Streptococcus agalactiae, Escherichia coli, Mycoplasma bovis,* and *Candida albicans.* In particular, when the milk-producing glands and surrounding tissue in the udder become infected, the tissue becomes inflamed with cellular infiltrates and associated toxins. The cellular infiltrates and associated toxins can cause a dramatic reduction in the quality of milk produced by an infected dairy animal. The quantity of milk produced is also usually affected, sometimes resulting in a total stoppage of production.

Occasionally, an infection will spread systematically to other organ and tissue sites via the blood or lymphatic systems. The spreading infection can, in extreme cases, seriously debilitate or kill the infected animal.

One effective way to control or prevent mastitis is by killing the pathogenic organisms which might otherwise infect the teat and udder tissues before the organism enters the tissues. This is accomplished by disinfecting the teats of the dairy animal both before and after milking with a topical antiseptic composition commonly known as a "teat dip." Such compositions kill or reduce the number of microorganisms on the teat surface before the microorganisms can migrate or be propelled during milking into the teat canal, or enter the teat via lesions or injuries. In fact, more than 50% of new udder infections can be prevented by disinfecting teats with an effective product immediately before or after every milking.

In addition to disinfecting teats immediately after milking, use of good milking and environmental management procedures, use of properly functioning milking equipment, and early identification and treatment or management of mastitis cases are part of an effective mastitis control plan. However, post-milking teat disinfection is the single most effective practice to reduce the rate of intramammary infection by contagious pathogens, such as *Staph. aureus.* In addition, a degree of control over environmental pathogens, such as *E. coli,* is exerted.

The present invention relates to an antiseptic teat dip comprising iodine as an antimicrobial agent. Current antiseptic teat dips containing iodine are iodophors. For the purposes of this invention, an iodophor is defined as a complex of iodine and a carrier molecule, such a non-ionic ethoxylated surfactants, cationic surfactants, poloxamers and polyvinylpyrrolidone (PVP). The complexed form of iodine, or iodophor, is not itself germicidal. Instead, it is $I_2$, or free iodine, that has the germicidal properties. Higher levels of free iodine in any given solution tend to allow for a quicker and more effective kill of microorganisms. In solution, the complexed iodine is in equilibrium with free iodine. As the free iodine is depleted, more free iodine is released from its complex to maintain the equilibrium.

The equilibrium level of free iodine in iodophor-based teat dip compositions depends on many factors, including the concentration of available iodine and the type of complex used. "Available iodine" is the total amount of complexed and free iodine in the system that can be measured by titration with sodium thiosulfate. While normally a higher concentration of iodophor (higher available iodine) in the composition results in a higher concentration of free iodine being released, this is not always the case. For example, an iodophor of iodine complexed with PVP produces higher equilibrium levels of free iodine as it is diluted. As a result, iodine-PVP compositions having an available iodine concentration of 1.0% are less germicidal over short exposure periods than iodine-PVP compositions having an available iodine concentration of between 0.01% and 0.1%. In the PVP-iodine iodophors, the iodine is in the form of tri-iodide ($I_3$). Upon dilution, the PVP-iodine complex is weakened, thereby releasing free iodine and increasing the equilibrium level of free iodine. This is thought to be a result of the dispersion of micelleular aggregates.

When concentrated iodine-PVP compositions are diluted, more free iodine as a percentage of available iodine is released. For example, in an iodine-PVP composition diluted to a concentration of 0.001% available iodine (10 ppm), virtually all of the iodine is present as free iodine. We have found that the maxium amount of free iodine present in an iodine-PVP composition occurs when the available iodine is at a concentration of approximately 0.01% (100 ppm). In this system, approximately 30%, or 30 ppm of the available iodine is present as free iodine.

Other iodophors operate differently than iodine-PVP iodophors. We have found that for non-ionic type complexes, compositions having higher concentrations of available iodine contain more free iodine. Thus, the chemistry of iodophors and iodine is complex. In addition, there are other factors besides the type of iodophor complex used that may affect the amount of free iodine in a given composition, such as pH, temperature, levels of iodides and iodates, emollient type and concentration, and dilution with water.

We have found that higher levels of free iodine can increase the speed of germicidal activity, especially for certain types of iodine complexes. Speed of germicidal activity is important for teat dip formulations, because the formulation may be on the animal's teat for only a limited period of time before it is removed. It is desirable for a teat dip composition to have a free iodine level of at least 5–10 ppm of iodine in order to generate an acceptable speed of germicidal activity.

As stated above, in an iodophor composition, the free iodine concentration is in equilibrium with the iodine complex. Thus, as the free iodine is depleted, more is produced from the remaining iodine complex. Because iodine is a highly reactive oxidizing agent, it will react with a wide variety of molecules. In addition, elemental iodine in solution is quite volatile. As a result, the available iodine may be depleted prior to completion of the antiseptic process. This is a problem with iodophor teat dips. Also, dilute preparations of iodophors are unstable over time, because of the relatively high levels of free iodine present at equilibrium. These two characteristics result in the unsuitability of dilute iodophor preparations as teat dips. Conventional concentrated iodophor teat dip compositions are also unsuitable because of irritation problems in the animals being treated resulting from the high iodine levels in the composition.

Therefore, formulating an effective teat dip, even under laboratory conditions, is challenging. This challenge is multiplied by the environment in which these compositions are actually used. Not only are the animal's teats physically stressed due to the repeated handling and milking, but the teats are also chemically stressed due to the repeated use of chemical teat dips and udder washes. In addition, the teats are subjected to environmental stress, such as cold, windy and dry conditions in the winter and the sun exposure in the summer. For example, water-based teat dips can freeze on the teat skin after application in cold, windy conditions, contributing to teat chapping or even frostbite. Such damage to the teats promotes colonization of microorganisms, which, in turn leads to a higher incidence of mastitis. Thus, many in the dairy industry do not use teat dip on their animals in such conditions. Moreover, on a daily basis, the teats are subjected to potentially high levels of pathogenic microorganisms from a variety of sources including the milking machines, soil, bedding, water, other animals, and the air. As stated above, teat skin that is damaged and/or stressed is more susceptible to colonization with mastitic microorganisms.

Therefore, iodine teat dip compositions have been developed that contain components at sufficiently high levels to effectively protect, heal and/or condition the teat skin. For example, U.S. Pat. No. 4,012,504 discloses a teat dip composition made by dissolving up to 7% by weight crystalline iodine in an animal or vegetable oil, specifically mineral oil, at an elevated temperature, and allowing the composition to cool. The '504 patent further discloses that preferably from about 0.2% to about 2% by weight iodine should be used. Theoretically, the amount of free iodine in such a composition should be quite high, limited only by the solubility of the iodine in mineral oil. This is in fact the case, as shown in Table 1, which lists the amount of free iodine resulting from various iodophor compositions, as well as the amount of free iodine resulting from an iodine/mineral oil and an iodine/water composition. The amount of free iodine for each composition was determined by dialysis, at 24 hours after preparation and after 216 hours for iodine/mineral oil and iodine/water.

The dialysis procedure was as follows:

100 ml of acidified water (water adjusted to a pH of 4–5 with phosphonic acid) was measured into a glass widemouth container. 50 ml of the sample to be analyzed was then placed in a polyethylene bag, and the bag was placed in the acidified water, with the sample portion submerged. The container was then allowed to stand for 16–24 hours at ambient temperature to reach equilibrium. 9 ml of acidified water was then removed from the container and mixed with 1 ml of a 1M KI solution. The mixed solution was then transferred to a cuvette and its absorbance was measured at 353 nm on a spectrophotometer against an acidified water reference sample. A standard iodine solution was then prepared by dissolving 0.30 g of iodine in 1000 ml of deionized water. The percentage of available or titratable iodine was determined using a standard 0.01 N sodium thiosulfate solution titration. 1 ml of the standard iodine solution was then mixed with 10 ml of 1M KI and 89 ml of acidified water, and the absorbance of this solution at 353 nm was determined. The amount of free iodine in the sample was then calculated using the following equation:

$$I_F = A_1 \times (V_s/V_a) \times (I_s/A_2)$$

where $I_F$ is ppm of free iodine in sample; $A_1$ is the net absorbance of sample; $V_s$ is total sample volume; $V_a$ is the volume of additional water in sample; $I_s$ is ppm of free iodine in standard solution; $A_2$ is the net absorbance of standard solution.

TABLE 1

Free Iodine Determination - Dialysis Method

| COMPOSITION | FREE IODINE (PPM) |
|---|---|
| After 24 hours | |
| 0.7% iodine-Mineral oil[1] | 113.6 |
| 0.7% iodine-water | 63.3 |
| 0.1% non-ionic iodophor | 2.9 |
| 0.25% non-ionic iodophor | 3.2 |
| 0.5% non-ionic iodophors (average) | 15.2 |
| 1.0% non-ionic iodophors (average) | 17.8 |
| 1.0% non-ionic iodophors w/10% glycerin (average) | 10.1 |
| 0.036% PVP iodophor | 13.8 |
| 0.055% PVP iodophor | 12.2 |
| 0.103% PVP iodophor | 9.4 |
| 0.516% PVP iodophor | 4.0 |
| 0.930% PVP iodophor | 2.8 |
| After 216 Hours | |
| 0.7% iodine-Mineral oil | 107.1 |
| 0.7% iodine-water | 10.6 |

[1]Percent iodine is the amount of available iodine in the composition

As can be seen in Table 1 and as stated above, iodine-PVP complexes show increased free iodine concentration as the amount of available iodine decreases, while the non-ionic ethoylated iodophors show just the opposite—that free iodine increases with increasing available iodine concentration.

Although the composition of the '504 patent (iodine/mineral oil) has a high level of free iodine, it is not germicidally effective in the laboratory or in the field under actual use conditions. One explanation for the ineffectiveness of this composition might be that the hydrophobic nature of the mineral oil prevents much of the iodine from actually reaching the microorganisms to be killed.

In the '504 patent, mineral oil was used as the carrier, or solvent, for the iodine. Iodophors have also contained emollients and humectants in relatively small amounts in an attempt to condition teat skin. The prevailing view, however, is that the germicidal activity of teat dip compositions may be reduced if the concentration of emollients in the composition is greater than 10% to 12% by weight. Pankey et al., J. Dairy Sci., 67:1336 (1984). For example, as shown in Table 1, a non-ionic iodophor composition comprising 1.0% available iodine has 17.8 ppm free iodine, which the same composition having 10% glycerin added has only 10.1 ppm free iodine. The conclusion is that this and other iodine compositions may be less stable when teat conditioners, such as emollients and humectants, are present.

Therefore, there is a need for an iodine-based teat dip composition that is effective as a germicide in short teat skin contact times, and also is a protecting and/or a healing agent for skin. There is also a need for an iodine-based teat dip composition that is stable over relatively long periods of time. There is a further need for an iodine-based teat dip composition that is highly efficacious, but is non-irritating in use. There is a yet another need for an iodine-based teat dip composition that can be used effectively to treat and/or prevent mastitis in a variety of weather conditions, and will not freeze in cold and windy weather. There needs are met by the teat dip composition of the present invention.

SUMMARY OF THE INVENTION

An iodine-based teat dip composition that is an effective germicide in short teat skin contact times, and additionally, is a protecting and/or healing agent for teat skin has been discovered. Surprisingly, and contrary to the conventional wisdom in the art, we have found an effective and non-irritating teat dip comprising iodine and significant amounts of propylene glycol. The teat dip composition of the present invention comprises from about 0.1% to about 2.% iodine by weight of the composition on a formulation basis and from about 50% to about 99.9% propylene glycol by weight of the composition. Using an amount of iodine between about 0.1% and 2% by weight of the composition on a formulation basis will yield a comparable amount of available iodine in the composition after formulation is complete.

The teat dip composition of the present invention may further comprise water and/or iodides and iodates, as well as other components conventionally found in teat dip compositions, such as dyes and wetting agents. While not wishing to be bound to any particular theory, it is believed that the present invention is stable, non-irritating and effective because the iodine forms a complex with the propylene glycol, although the complex is in all probability of a different nature than that formed in known iodophors, such as PVP or non-ionic ethoxylates.

The teat dip composition of the present invention is unique in its ability to deliver unusually high levels of germicidal free iodine while retaining high levels in reserve, to be non-irritating to skin, to be shelf-stable, and provide a high degree of skin conditioning and protection from freezing due to its high level of emollients. The present invention is unlike more concentrated iodophors which may have low levels of free iodine at any given time and also tend to be more irritating to the skin, especially when used prolonged periods of time.

This invention is also unlike concentrated iodophors that are freshly diluted or iodophors that are sold already diluted, because the teat dip of the present invention has high levels of free iodine while retaining considerable available iodine in reserve. This invention is unlike tinctures and other aqueous mixtures of elemental iodine because it has sufficient shelf-stability and is non-irritating to skin. In fact, because of its high levels of emollients, the teat dip composition of the present invention is non-irritating and beneficial as a skin conditioner. In addition, it is able to protect teat skin under cold and windy conditions and thereby helps prevent chapping and frostbite, which can lead to higher levels of mastitis.

Further objects, features and advantages of the invention will be apparent from the following detailed description.

DESCRIPTION OF THE PREFERRED EMBODIMENTS

The teat dip composition of the present invention comprises iodine in an amount of from about 0.1% to about 2% by weight of the composition on a formulation basis. "Formulation basis" means the amount of iodine used in formulating the composition. For example, a composition made by combining 1 part (by weight) iodine and 99 parts other ingredients containing 1% iodine by weight on a formulation basis. At iodine amounts less than about 0.1% on a formulation basis, the shelf life of the composition starts to suffer, while at amounts over about 2% on a formulation basis, the iodine begins to precipitate out of the solution. More preferably, iodine is present in an amount of from about 0.5% to about 1% by weight of the composition on a formulation basis. This amount of iodine provides a composition having optimal stability, shelf life and germicidal efficacy.

The iodine is preferably provided by the use of elemental iodine. The amount of iodine in the composition may also be measured on an "available iodine" basis rather than a formulation basis. As stated previously, available iodine is determined using a standard titration procedure comprising titrating a sample of the composition with sodium thiosulfate. A teat dip composition of the present invention comprising iodine in an amount of from about 0.1% to about 2% by weight of the composition on a formulation basis will contain a comparable amount of available iodine. If this method of iodine measure is used, the compositions of the present invention should comprise from about 0.1% to about 2% available iodine by weight of the composition, with the preferred amount of available iodine being from about 0.5% to about 1% by weight of the composition.

The amount of iodine in the compositions of the present invention can also be determined on a "free iodine" basis, using the method disclosed previously. If this method of iodine measurement is used, the compositions of the present invention should comprise at least 5 parts per million ("ppm") free iodine. Preferably, the compositions should comprise from about 5 ppm to about 100 ppm free iodine.

The teat dip composition of the present invention also contains propylene glycol as the primary carrier for the iodine. The propylene glycol is present in an amount of from about 50% to about 99.9% by weight of the composition on a formulation basis. More preferably, propylene glycol is present in an amount of from about 70% to about 90% by weight of the composition on a formulation basis.

The composition of the present invention may also comprise water. As stated earlier, the use of water in certain iodine-based teat dip compositions results in higher levels of free iodine being present at equilibrium than if water is not used. The composition of the present invention is apparently one of those systems, as can be seen in Table 2, which shows the amount of free iodine for certain compositions of the present invention. The free iodine concentration was determined by the dialysis method, as set forth previously.

TABLE 2

| COMPOSITION | FREE IODINE (PPM) |
|---|---|
| After 24 Hours | |
| 0.7% iodine-Propylene glycol (no water)[1] | 14.9 |
| 0.7% iodine-Propylene glycol (25.0% water) | 96.7 |
| 0.7% iodine-Propylene glycol (30% water) | 107.7 |
| After 216 Hours | |
| 0.7% iodine-Prop glycol (no water) | 19.1 |
| 0.7% iodine-Prop glycol (25.0% water) | 106.8 |
| 0.7% iodine-Prop glycol (30% water) | 106.4 |

[1]Percent iodine is available iodine.

As shown in Table 2, a teat dip composition of the present invention comprising 0.7% available iodine by weight of the composition and 99.3% propylene glycol generated 14.9 ppm of free iodine. In contrast, compositions comprising the same amount of available iodine, but containing either 74.3% propylene glycol and 25.0% water on a formulation basis or 69.3% propylene glycol and 30% water on a formulation basis generated 96.7 ppm free iodine and 107.7 ppm free iodine, respectively. Although the teat dip of the present invention containing no water has effective germicidal action, the use of water in an amount of from about 0.1% to about 50% by weight of the composition on a formulation basis is preferred. More preferably, water should be present in an amount of from about 20% to about 40% by weight of the on a formulation basis.

The ratio of water and propylene glycol in the system can composition be adjusted to provide a desired amount of free iodine for a given amount of available iodine in the composition.

Other sources of free iodine, such as iodides and iodates can also be present in the teat dip composition of the present invention. Iodide may be present in an amount of from about 0.05% to about 1.0% by weight of the composition on a formulation basis. More preferably, iodide may be present in an amount of from about 0.1 % to about 0.3% on a formulation basis. The use of iodides in the composition is preferred. Iodates, if desired, may be present in an amount from about 0.05% to 1.0% by weight of the composition on a formulation basis. If iodates are used, an amount of from about 0.1% to about 0.3% by weight on a formulation basis is preferred.

Additional components may also be present in the teat dip composition of the present invention, such as dyes or colorants and wetting agents. The dyes of colorants should be present in an amount from about 0.01% to 0.05% by weight of the composition on a formulation basis, while wetting agents should be present in an amount from about 0.05% to about 0.15% by weight of the composition on a formulation basis.

The teat dip compositions of the present invention can be prepared by dissolving elemental iodine in propylene glycol. Dissolution can be accomplished by agitating the mixture for approximately 10 to 16 hours at room temperature. After all the iodine is dissolved, additional components, such as water, colorants, dyes, wetting agents, iodide, and iodate are added with stirring.

The teat dip composition of the present invention can be used to prevent mastitis in dairy animals by topical application of the compositions to the teats of the animals. The composition can be applied to the teats by dipping or spraying, and may be used both before and after milking. The composition of the present invention should not be diluted for use and otherwise may be used in the same manner as conventional teat dips.

The antiseptic teat dip compositions of the present invention have impressive efficacy against a variety of mastitis-causing gram-positive and gram-negative bacteria, both in the laboratory and in actual use in the field, as shown by the following Examples.

EXAMPLE 1

A teat dip composition of the present invention comprising 0.6% available iodine, 74.4% propylene glycol, and 25.0% water by weight of the composition was formulated as described above, and tested for germicidal activity against *Staph. aureus* and *E. coli,* two mastitis-causing organisms. Suspensions containing the above microorganisms were exposed to the composition of the present invention, as well as other test compositions, for a given length of time. Residual germicide in the compositions was then neutralized with a quenching solution. Surviving bacteria were then plated and enumerated using the plate count method.

The results for the various compositions versus *Staph. aureus* and *E. coli* are shown in Tables 3 and 4, respectively, where CFU is colony-forming units.

TABLE 3

| Treatment Composition | CFU/ml | % Survival |
|---|---|---|
| *Staph. aureus* ATCC #6538 | | |
| Negative Control | $1.29 \times 10^8$ | — |
| 1.0% $I_2$-non-ionic ethoxylate[1] | <2.5 | 0 |
| 0.9% $I_2$-non-ionic ethoxylate | $9.20 \times 10^5$ | 0.71% |
| 0.4% $I_2$-non-ionic ethoxylate | $1.3 \times 10^3$ | 0.001% |
| 0.4% $I_2$-non-ionic ethoxylate | $3.88 \times 10^3$ | 0.003% |
| Chlorine dioxide/chlorus acid | $1.53 \times 10^3$ | 0.001% |
| 0.6% $I_2$-Propylene Glycol | 2.5 | 0 |
| 0.6% $I_2$-Mineral Oil | $6.10 \times 10^4$ | 0.047% |

[1]Percent iodine is available iodine

TABLE 4

| Treatment Composition | CFU/ml | % Survival |
|---|---|---|
| *E. coli* ATCC #25922 | | |
| Negative Control | $1.56 \times 10^7$ | — |
| 1.0% $I_2$-non-ionic ethoxylate[1] | 2.5 | Sta |
| 0.9% $I_2$-non-ionic ethoxylate | 5.0 | 0 |
| 0.4% $I_2$-non-ionic ethoxylate | $3.50 \times 10^5$ | 2.24% |
| 0.4% $I_2$-non-ionic ethoxylate | $1.98 \times 10^5$ | 1.27% |
| Chlorine dioxide/chlorous acid | <2.5 | 0 |
| 0.6% $I_2$-Propylene Glycol | 45 | 0 |
| 0.6% $I_2$-Mineral Oil | $2.41 \times 10^7$ | 154.49% |

[1]Percent iodine is available iodine.

The teat dip composition of the present invention was extremely effective against both *Staph. aureus* and *E. coli*, killing essentially all of the organisms. Indeed, it was as effective as the iodine/non-ionic ethoxylate iodophor compositions containing 0.9%–1.0% available iodine. Notably, although an iodine/mineral oil composition has high free iodine (see Table 1), the iodine/mineral oil composition tested in the suspension assay, which contained the same amount of available iodine was totally ineffective against *E. coli*.

EXAMPLE 2

A teat dip composition of the present invention comprising 0.6% available iodine and 74.4% propylene glycol, and 25.0% water by weight of the composition was formulated as described above, and was tested in a suspension assay against *Staph. aureus* and *E. coli,* using the procedure of Example 1. Where indicated below, the composition of the present invention, along with several of the other test compositions, was diluted with an equal amount of milk, to simulate field conditions, where teat dips are frequently "diluted" from leaking milk on the teats, more accurately. The results are shown below in Tables 5 and 6.

TABLE 5

| Treatment Composition | CFU/ml | % Survival |
|---|---|---|
| *Staph. aureus* ATCC #6538 | | |
| Negative Control | $2.36 \times 10^8$ | — |
| 0.5% available $I_2$-non-ionic ethoxylate w/50% milk | 5 | 0% |
| 0.5% $H_2O_2$-no milk | <2.5 | 0% |

TABLE 5-continued

| Treatment Composition | CFU/ml | % Survival |
|---|---|---|
| 0.5% $H_2O_2$ w/50% milk | $4.75 \times 10^2$ | 0.0002% |
| Composition of the invention w/50% milk | <2.5 | 0% |

TABLE 6

| Treatment Composition | CFU/ml | % Survival |
|---|---|---|
| *E. coli* ATCC #25922 | | |
| Negative Control | $2.15 \times 10^7$ | — |
| 0.5% available $I_2$-non-ionic ethoxylate w/50% milk | $1.15 \times 10^2$ | 0.00053% |
| 0.5% $H_2O_2$-no milk | <2.5 | 0% |
| 0.5% $H_2O_2$ w/50% milk | <2.5 | 0% |
| Composition of the invention w/50% milk | 15 | 0.00006% |

Again, the composition of the present invention was extremely efficacious against both *Staph. aureus* and *E. coli*.

EXAMPLE 3

Two teat dip compositions of the present invention, one comprising approximately 0.6% available iodine, 74.4% propylene glycol and 25.0% water by weight, and the other comprising approximately 0.7% available iodine and 74.3% propylene glycol and 25.0% water by weight, that were formulated as above, were tested in an Excised Teat Assy to determine the speed at which the compositions kill *Staph. aureus* and *E. coli*. Certain commercially available teat dip compositions were also tested. Excised cow teats were exposed to bacteriological cultures, then to the test compositions for a time period of 10 minutes, 30 seconds or 5 seconds. Residual germicide was neutralized via quenching, and the surviving microorganisms were collected and enumerated using the plate count method. The results are shown in Table 7 (*Staph. Aureus*) and Table 8 (*E. coli*). In Table 8, the amount of iodine tested under the heading "Treatment Composition" is percent available iodine (approximated). As shown, free iodine was also calculated for some compositions.

TABLE 7

| Treatment Composition | % Avail. Iodine | CFU/ml | Log Red. | % Log Red. |
|---|---|---|---|---|
| *Staph. aureus* ATCC #27543 | | | | |
| Negative Control | — | $6.75 \times 10^6$ | — | — |
| 0.5% available $I_2$-non-ionic ethoxylate (30 second exposure) | 0.558% | $2.10 \times 10^5$ | 2.51 | 27.5% |
| 0.5% available $I_2$-non-ionic ethoxylate (5 second exposure) | 0.558% | $1.92 \times 10^5$ | 2.55 | 27.9% |
| Composition of the invention (30 seconds) | 0.609% | $1.78 \times 10^5$ | 2.58 | 28.3% |
| Composition of the invention (5 seconds) | 0.609% | $1.78 \times 10^5$ | 2.58 | 28.3% |
| 0.5% $H_2O_2$ (30 seconds) | | $2.45 \times 10^5$ | 2.44 | 26.7% |
| 0.5% $H_2O_2$ (5 seconds) | | $1.64 \times 10^5$ | 2.61 | 28.6% |

TABLE 7-continued

| Treatment Composition | % Avail. Iodine | CFU/ml | Log Red. | % Log Red. |
|---|---|---|---|---|
| Iodine-Mineral Oil (10 minutes) | 0.571% | $7.47 \times 10^5$ | 1.96 | 21.5% |
| Composition of the invention (10 minutes) | 0.698% | $1.22 \times 10^3$ | 4.74 | 51.9% |

TABLE 8

| Treatment Composition | Free Iodine | CFU/ml | Log Red. | % Log Red. |
|---|---|---|---|---|
| *E. coli* ATCC #25922 | | | | |
| Negative Control | — | $1.55 \times 10^6$ | — | — |
| 0.5% available $I_2$-non-ionic ethoxylate (30 second exposure) | not calculated | $6.56 \times 10^4$ | 1.37 | 18.3% |
| 0.5% available $I_2$-non-ionic ethoxylate (5 second exposure) | not calculated | $1.26 \times 10^5$ | 1.09 | 14.6% |
| Composition of the invention (0.6% I2) (30 seconds) | not calculated | $4.44 \times 10^4$ | 1.54 | 20.6% |
| Composition of the invention (0.6% I2) (5 seconds) | not calculated | $4.26 \times 10^4$ | 1.56 | 20.8% |
| 0.5% $H_2O_2$ (30 seconds) | | $1.58 \times 10^5$ | 0.99 | 13.2% |
| 0.5% $H_2O_2$ (5 seconds) | | $3.27 \times 10^5$ | 0.67 | 8.9% |
| Iodine-Mineral Oil (10 minutes) | 113.6 ppm | $1.53 \times 10^5$ | 1.00 | 13.4% |
| Composition of the invention (0.6% I2) (10 minutes) | 9.67 ppm | $2.39 \times 10^3$ | 2.79 | 37.2% |
| Iodine-deionized water (10 minutes) | 63.6 ppm | $1.25 \times 10^5$ | 1.09 | 14.6% |

The above results indicate that the teat dip compositions of the present invention are efficacious against both *Staph. aureus* and *E. coli*, even under short exposure times.

EXAMPLE 4

The teat dip compositions of the present invention were also analyzed to determine the degree of irritation they would cause in use on the teats of dairy animals. Teat dip compositions comprising from about 0.5% to 0.75% available iodine, about 74.25% propylene glycol, and about 25.0% water by weight of the composition were subjected to a high sensitivity dermal irritation test using a kit made for that purpose, available from In-Vitro International, 16632 Millikan Ave., Irvine, Calif., along with some commercially available teat dips. The test measures a given sample composition's propensity to degrade a biomembrane barrier and a macromolecular matrix. Known skin irritants are used as controls in the test, and are compared against the sample compositions to provide a relative assessment of the sample composition's likelihood to produce skin irritation in use. The results, which document two separate tests, are shown in Tables 9 and 10, where "HQD" is the highest qualified dose, and "PDII" is the primary dermal irritation index.

TABLE 9

| Test Composition | HQD | PD II SCORE | CLASSIFICATION |
|---|---|---|---|
| Chloride dioxide/chlorous acid | 200 ul | >1.20 | High Irritant |
| Chloride dioxide/chlorous acid | 200 ul | 1.18 | High Irritant |
| 0.5% available I$_2$-non-ionic ethoxylate | 200 ul | 0.30 | Low Irritant |
| Composition of the invention | 200 ul | 0.35 | Low Irritant |
| 0.5% H$_2$O$_2$ | 200 ul | >1.20 | High Irritant |
| Chloride dioxide/chlorous acid | 100 ul | 0.72 | Intermediate-High |
| Chloride dioxide/chlorous acid | 100 ul | 0.40 | Low Irritant |
| 0.5% available I$_2$-non-ionic ethoxylate | 100 ul | 0.08 | Non-Irritant |
| Composition of the invention | 100 ul | 0.11 | Non-Irritant |
| 0.5% H$_2$O$_2$ | 100 ul | 1.10 | High Irritant |

TABLE 10

| Test Composition | HQD | PD II SCORE | CLASSIFICATION |
|---|---|---|---|
| Chloride dioxide/chlorous acid | 200 ul | >1.20 | High Irritant |
| Chloride dioxide/chlorous acid | 200 ul | 1.15 | High Irritant |
| 0.5% available I$_2$-non-ionic ethoxylate | 200 ul | 0.40 | Low Irritant |
| Composition of the invention | 200 ul | 0.32 | Low Irritant |
| 0.5% H$_2$O$_2$ | 200 ul | 1.18 | High Irritant |
| Chloride dioxide/chlorous acid | 100 ul | 0.98 | Intermediate-High |
| Chloride dioxide/chlorous acid | 100 ul | 0.55 | Low Irritant |
| 0.5% available I$_2$-non-ionic ethoxylate | 100 ul | 0.13 | Non-Irritant |
| Composition of the invention | 100 ul | 0.16 | Non-Irritant |
| 0.5% H$_2$O$_2$ | 100 ul | 1.07 | High Irritant |

The teat dip compositions of the present invention are thus substantially non-irritating in use.

EXAMPLE 5

A teat dip composition of the present invention was tested in a controlled infection trial to determine its efficacy for preventing intramammary infection ("IMI"), or mastitis, with *Staph. aureus* and *Strep. agalactiae*. The trial was carried out using the general procedures recommended by the National Mastitis Council and according to the procedure of Hogan, J. S., Galton, D. M., Harmon, R. J., Nickerson, S. C., Oliver, S. P., Pankey, J. W., "Protocols for Evaluation of the Efficacy of Post-Milking Teat Dips." *J. Dairy Sci* 73:2580 (1990), as follows.

At the initiation of the trial, the cows to be used in the study were pre-screened for existing infection to ensure that only healthy cows were being used in the trial. At the afternoon milking, Monday through Friday, the lower third of all four teats of each of the 58 cows in the study was exposed on a suspension containing both *Staph. aureus* (Newbould 305) and *Strep. agalactiae* (McDonald 44) immediately after the milking machines were removed. Within 5 to 10 seconds thereafter, two teats (right front, left rear) were dipped full length with a teat dip composition comprising about 0.5% available iodine by weight of the composition and about 74.25% propylene glycol, and about 25.0% water by weight of the composition. The remaining two teats served as undipped controls.

Milk samples from each cow were then collected and analyzed weekly during the trial. In instances where *Staph. aureus* or *Strep. agalactiae* were present for the first time in a previously uninfected teat, a second sample was collected immediately and cultured. All teats were eligible for new infections during the trial except those infected with organisms of the same species as the challenge organisms, and those with deformed or abnormal teats.

The teat end and teat skin condition in both dipped and undipped teats were evaluated immediately before the trial started and at the conclusion of the trial to determine any effects of the teat dip composition on the condition of the teat ends and lateral teat skin. The teats were evaluated for chapping, cracks, and other forms of irritation.

The results of the trial are set forth below in Table 11.

TABLE 11

| Organism and treatment | Quarters eligible for new IMI | New IMI Week | | | | | | | | | Total | % Quarters | Reduction |
|---|---|---|---|---|---|---|---|---|---|---|---|---|---|
| | | 1 | 2 | 3 | 4 | 5 | 6 | 7 | 8 | 9 | | | |
| *Staph aureus* | | | | | | | | | | | | | |
| Dip | 109 | 0 | 0 | 1 | 0 | 1 | 0 | 0 | 0 | 0 | 2 | 1.8 | |
| Control | 108 | 0 | 0 | 7 | 0 | 10 | 3 | 3 | 1 | 1 | 25 | 23.1 | 92.0* |
| *Strep. Agalactiae* | | | | | | | | | | | | | |
| Dip | 115 | 3 | 0 | 0 | 0 | 1 | 2 | 0 | 2 | 1 | 9 | 7.8 | |
| Control | 115 | 3 | 0 | 1 | 0 | 2 | 2 | 2 | 5 | 2 | 17 | 14.8 | 47.1** |

*Significant, P < 0.001.
**Not Significant, P < 0.10.

These results show that the compositions of present invention reduced the infection rate for *Staph. aureus* by over 90%, and reduced the infection rate for *Strep. agalactiae* by almost 50%. In addition, there were no adverse effects on the condition of the teats resulting from the use of the composition of the present invention.

It is understood that the invention is not limited to the particular construction and arrangements of parts herein illustrated and described, but embraces such modified forms thereof as come within the scope of the following claims.

The invention claimed is:

1. A teat dip composition comprising from about 0.5% to about 2% available iodine by weight of the composition on a formulation basis, at least about 50% propylene glycol by weight of the composition on a formulation basis, iodide present in an amount from about 0.05% to about 1.0% by weight of the composition on a formulation basis, and iodate present in an amount from about 0.05% to about 1.0% by weight of the composition on a formulation basis.

2. The teat dip composition of claim 1, further comprising from about 10% to about 30% water by weight of the composition on a formulation basis.

3. A method of treating mastitis, comprising the step of:

topically applying the teat dip composition of claim 1 in an effective amount to the teats of a dairy animal.

* * * * *